United States Patent [19]

Compton et al.

[11] 4,323,193

[45] Apr. 6, 1982

[54] WICK-TYPE SLOW DIFFUSION DISPENSER

[75] Inventors: Donald B. Compton, Montgomery; William P. Lewis, West Chester; Toan Trinh, Maineville, all of Ohio

[73] Assignee: The Procter & Gamble Company, Cincinnati, Ohio

[21] Appl. No.: 92,905

[22] Filed: Nov. 9, 1979

Related U.S. Application Data

[63] Continuation-in-part of Ser. No. 92,169, Nov. 7, 1979.

[51] Int. Cl.³ ............................................. A24F 25/00
[52] U.S. Cl. ........................................................ 239/44
[58] Field of Search ............................ 239/44, 47, 51.5

[56] References Cited

U.S. PATENT DOCUMENTS

| | | |
|---|---|---|
| 1,043,159 | 11/1912 | Sleeper . |
| 1,839,357 | 1/1932 | Thorson . |
| 2,529,536 | 11/1950 | Bjorksten . |
| 2,710,825 | 6/1955 | Lazier . |
| 2,905,591 | 9/1959 | Bulloff . |
| 2,927,055 | 3/1960 | Lanzet . |
| 3,679,133 | 7/1952 | Sekiguchi . |
| 3,821,413 | 6/1974 | Hellyer . |
| 3,903,022 | 9/1975 | Ohara . |

Primary Examiner—Richard A. Schacher
Attorney, Agent, or Firm—Leonard Williamson; Ronald L. Hemingway; Richard C. Witte

[57] ABSTRACT

An improved liquid material dispenser of the type which transmits fluid to be diffused from an enclosed reservoir to an exposed evaporative surface by means of a wick. A wick is provided in the form of a sheet which has a very high evaporative area compared to the volume of liquid which is retained outside the confines of the reservoir at a given time. The critical relation of evaporation area to volume of liquid outside the reservoir is such that the exposed liquid material weight per square centimeter of evaporative surface is less than 10 milligrams per square centimeter. The material to be dispensed, preferably a perfume, comprises at least 50% of materials of no more than moderate volatility as defined herein. Materials having low volatility as defined herein are minimized, and the quantity of low volatility ingredients in said liquid materials is related herein to the holding capacity of the evaporative surface of the wick. The combination of the improved dispenser and improved liquid materials to be diffused maintains the evaporating liquid material at a relatively constant composition, and the liquid material evaporates at a relatively steady rate over the life of the dispenser.

6 Claims, 2 Drawing Figures

WICK-TYPE SLOW DIFFUSION DISPENSER

CROSS REFERENCE TO RELATED APPLICATION

This application is a continuation-in-part of U.S. Ser. No. 092,169, filed by the present inventors on Nov. 7, 1979.

FIELD OF THE INVENTION

Most broadly the invention is a dispenser for the slow diffusion of a fluid to the ambient air, the dispenser being of the type which employs a wick to transfer the operating fluid from an enclosed reservoir to an evaporative surface which is in contact with the ambient atmosphere. These dispensers are adapted to be used to diffuse a multicomponent liquid material such as a perfume which is formulated so that nearly all of its components are of similar volatility.

The invention relates more specifically to wicks for the described dispensers which maximize the area of the evaporative surface, and maximize the rate of wicking of fluids to the evaporative surface, while minimizing the quantity of perfume or other liquid material which is exposed to the ambient atmosphere at a given time. This limitation allows the transpired liquid material to be more constant in composition as it is depleted from the reservoir during the useful life of the dispenser.

BACKGROUND ART

Dispensers for liquid materials which employ a wick in order to conduct the liquid material from a reservoir which is isolated from the atmosphere to an evaporating surface which is exposed to the atmosphere have long been known to the art. However, those skilled in the art have not previously taught that in such dispensers the amount of liquid material exposed to the atmosphere outside the dispenser at a given time should be minimized, while the area of the evaporative surface of the wick should be maximized. Thus, while the basic prior art dispenser construction may suffice for the diffusion of fluids which comprise a single component, or an azeotropic mixture of materials which evaporate uniformly, several problems have been noted in the art which prevent the prior art devices from realizing the goal of uniform diffusion over a long period of time when the liquid material to be diffused is a multi-component liquid. This problem is particularly noted in the perfume art, in which multi-component liquids are commonly used.

A major problem with dispensers of the prior art, when used to dispense liquids having multiple components of differing volatility, is that the material dispensed at a given time changes in amount and character during the life of the dispenser. This result is obtained because when the liquid material to be dispensed is exposed to air, the more volatile constituents of the liquid material rapidly evaporate and become depleted while the dispenser is in use, so that in the early stages of operation the dispenser diffuses a material which is rich in the more volatile constituents and relatively high in vapor phase concentration, while later in the life of the dispenser the rate of diffusion is much lower and the materials which are diffused are more prominently those which have a low evaporation rate. Examples of the prior art which raises this problem or related problems are as follows: U.S. Pat. No. 3,903,022, issued to Ohara et al. on Sept. 2, 1975 (perfume and sublimable substrate which evaporate at similar rates); U.S. Pat. No. 2,927,055, issued to Lanzet on Mar. 1, 1960 (formulation of perfumes having components which ordinarily volatilize at different rates with a novel gelling agent and water in order to level the rate of volatilization of the various perfume components); U.S. Pat. No. 2,710,825, issued to Lazier et al. on June 14, 1955 (teaches the selection of fragrance imparting ingredients of relatively low volatility for a perfume in order to give the diffused material a constant odor character over an extended evaporation period); U.S. Pat. No. 2,905,591, issued to Bulloff on Sept. 22, 1959 (perfume actives and carriers should be selected to have similar vapor pressures); U.S. Pat. No. 4,158,440, issued to Sullivan et al. on June 19, 1979 (components with different volatility are placed in separate dispensing means having compensating dispensing rates); and U.S. Pat. No. 3,679,133, issued to Sekiguchi et al. on July 25, 1972 (perfume is delivered to an evaporation surface under pressure, instead of by wicking, in order to avoid a change in the composition of the diffused material over time).

U.S. Pat. No. 3,821,413, issued to Hellyer, Jr., on June 28, 1974, teaches, particularly in Formulation 1 and the accompanying text and graph, that certain compositions may be formulated in which the proportion of a glycol in the evaporating mixture can be held constant over a period of time. It will be found upon close examination of the reference cited in Hellyer for boiling points that Formulation 1 contains a high proportion of ingredients which have boiling points similar to that of the propylene glycol in the formulation. Hellyer does not teach, however, that the boiling points of the mixture components are relevant to the favorable performance of the composition in maintaining a steady composition during evaporation.

Another problem noted in the prior art relating to dispensers used to diffuse multi-component liquids, and particularly perfumes, is that of wick blockage. When a dispenser of the type employing a wick is used to transpire perfumes over a long period of time, it is found that the rate of perfume delivery often falls off steadily because less volatile components, or the oxidation products of more volatile components, become concentrated in the exposed portion of the wick and block the transfer of fluids within the wick or diffusion of fluids (in vapor form) from the evaporative surface of the dispenser. The prior art discusses this problem and provides various solutions. U.S. Pat. No. 2,529,536, issued to Bjorksten on Nov. 14, 1950, teaches that wick blockage occurs as the components of low volatility in perfume compositions accumulate in the portions of the wick adjacent to the evaporative surface, and teaches that this problem may be alleviated by periodically inverting the wick so that the solvent materials in the reservoir can dissolve the blocking components and thus reverse the wick blockage. The Bulloff reference cited above teaches that perfumes which deposit gums and the like are not favored for use in wick-type dispensers, and further teaches that solid antioxidants should not be used in the perfume, as the solid materials may block the wick. Finally, the Sekiguchi reference cited above suggests that the problem of wick blockage may be alleviated by transferring perfume from the reservoir to the evaporative surface by means other than wicking.

Although the art has made some progress toward the goal of avoiding fractionation of perfumes by providing perfumes made of components with similar volatilities, it will be apparent that in many perfume applications the volatility of the perfume components cannot be so strictly regulated as to eliminate the problem of perfume fractionation.

The present inventors are not aware of any prior art which teaches what properties are needed in a wick-type dispenser system, and particularly in the wick itself, in order to reduce the fractionation of multi-component perfumes. Wicks in the form of sheets have been used in the air humidifying art in order to provide a high level of diffusion of water vapor to the ambient air, but these references do not address the problem of fractionation of a multi-component liquid as it is evaporated because the material to be evaporated is plain water. The relevant references in the humidifier art are U.S. Pat. No. 1,839,357, issued to Thorson et al. on Jan. 5, 1932; and U.S. Pat. No. 1,043,159, issued to Sleeper on Nov. 5, 1912. As with many other references relating to wick structure, these patents teach only that wicking rate is important, or that the ability to wick at all is important, and they do not teach that the amount of liquid material held outside the reservoir in the evaporative surface of the wick should be minimized.

Thus, a first object of the present invention is to provide a dispenser, especially adapted for the diffusion of multi-component liquids, which minimizes the fractionation of the liquid material over time so that the dispensed vapor is relatively constant in concentration and in quality during the useful life of the dispenser.

A second object of the present invention is to provide perfume compositions which are comprised primarily of components having similar levels of volatility, so as to further minimize the problem of uneven distribution of perfume materials during the useful lifetime of a perfume dispenser.

Still another object of the invention is to accomplish the above objectives in a liquid material dispenser which is sufficiently simple and inexpensive to be provided as a single use disposable dispenser.

Still another object of the present invention is to minimize the degradation of the liquid material by air-induced oxidation or polymerization in a wick-type diffusion dispenser.

The improvements in the present invention which satisfy one or more of the above objects of the invention are presented below.

DISCLOSURE OF THE INVENTION

The present invention is an improved wick-type dispenser employing a wick having a sheet form which provides a very large evaporative surface compared to the weight of liquid which is maintained in the evaporative surface, and thus exposed to the atmosphere, at a given time. The ratio of exposed liquid material weight to evaporative surface area is less than about 10 milligrams of liquid material per square centimeter of evaporative surface in the dispenser, preferably less than 7 milligrams of the liquid per square centimeter of evaporative surface. These modifications allow the effective transpiration of a multicomponent liquid (preferably a perfume) to the ambient atmosphere from a wick-type dispenser and minimize the changes in vapor character and concentration over time which are noted as problems in the prior art. Air-induced oxidation or polymerization of the perfume is also minimized in this structure.

In order to achieve the highly preferred result of liquid material transpiration at a nearly constant level and composition over a large portion of the life of a multicomponent liquid diffusion dispenser, the present invention also provides that at least 50%, and preferably 75%, of the liquid material components should be materials of no more than moderate volatility, and that the total quantity of low volatility ingredients in the dispenser should be no more than 34% by weight of the capacity of the wick for the multi-component liquid in its original form.

Several additional properties are highly desirable in a dispenser made according to the present invention, and, accordingly, preferred dispensers have one or more additional properties. A highly preferred wick for use herein is a single sheet of wick fabric having a basis weight of from 15 to 50 grams per square meter and an absorbency of about 1.75 to about 4.25 times its weight for the multicomponent liquid material to be dispensed. Preferred wicks provide an evaporative surface with a diffusion rate for the multi-component liquid which is substantially equal to the diffusion rate required in order to provide a preferred level of the multi-component liquid material in vapor form to the ambient atmosphere.

In even more preferred embodiments of the present invention the wick has a high vertical wicking height which reduces the horizontal extent of the wick needed in order to provide a particular effective evaporative surface area. Such highly preferred wicks also have the ability to wick fluid to about one-half of their final wicking height in about three minutes. This high initial wicking height insures that the dispensers of the present invention will rapidly reach their equilibrium state of operation when the dispenser is activated.

DETAILED DESCRIPTION OF THE INVENTION

Figure 1:
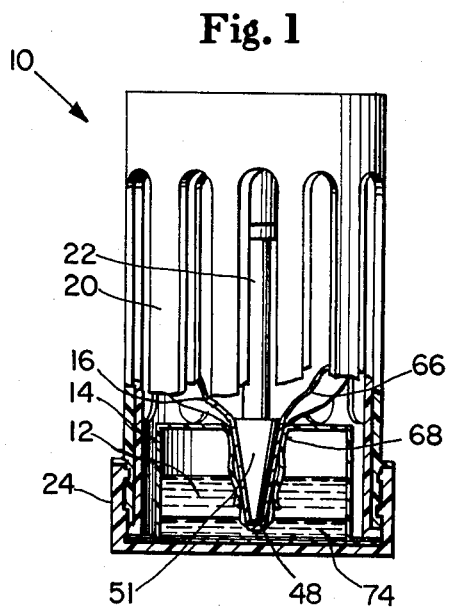
FIG. 1 is an elevational view of the subject liquid material diffusion dispenser partially broken away and sectioned to show the general arrangement of the elements of the dispenser in operation.

What follows is a detailed description of the present invention, and particularly a description of preferred embodiments which constitute the best mode of carrying out the present invention. This description exemplifies the present invention and points out several desired features of the dispensers made according to the present invention, but is not intended to limit the scope of the invention, which is delineated in the claims which conclude the specification.

In order to more completely describe the present invention, it is necessary to define several of the terms used herein, as follows:

The evaporative surface of a wick is defined as the total surface area of wick material which is exposed to the atmosphere when the dispenser is in use. The evaporative surface of a sheet of material is considered the combined surface area of both sides of the material if both sides are exposed to the atmosphere. If the total vertical wicking height of the wick (as defined below) is not sufficient that the wick is able to conduct the liquid material to be diffused to its entire surface, the evaporative surface of the wick is defined as that exposed surface area which is actually wet when the dispenser is in use.

The retention weight of the wick is the weight in milligrams of a liquid material supported per square centimeter of wick material when the wick is saturated. Retention weight is measured under the test conditions described later in this specification.

The total vertical wicking height of the wick is defined as the vertical extent to which the wick is able to raise the said liquid material above the liquid surface in the reservoir. The total vertical wicking height is measured by vertically suspending a strip of the wick material so that it is in contact with a bath of said liquid material to be dispensed. The test is conducted under conditions of low air circulation and the height of the head of liquid in the wick is measured after 18 hours. This test is described in greater detail below.

The initial wicking height is defined as the fraction of the total vertical wicking height which is attained within three minutes after the total vertical wicking height test is begun.

The total absorptive capacity of the wick is defined as the weight of the said liquid material which the wick can support when it is saturated with the material, expressed as a multiple of the dry wick weight.

The air permeability of the wick is defined as the volume of air which will pass through the dry wick per minute under the test conditions described in the air permeability test set forth later in the specification.

A multi-component liquid material is defined as any volatilizable liquid substance containing a substantial proportions of at least two components which have different volatilities or retention times as defined herein. Multi-component liquids as defined herein do not include azeotropic mixtures.

The volatility of a material is defined herein according to the retention time of the material in a gas chromatograph which is identified and operated according to the gas chromatograph retention time test described later in the specification. A material of low volatility (also called a "high boiler") is one which has a gas chromatograph retention time greater than 30 minutes; a liquid material of medium volatility is one which has a gas chromatograph retention time of from 16 to 30 minutes; and a material of high volatility, also called a "low boiler," is one which has a gas chromatograph retention time of less than 16 minutes.

The holding capacity of the diffusion area of a wick is defined as the product of the retention weight of the wick material and the diffusion area of the wick when it is in an operating dispenser. Holding capacity is measured in grams.

The Dispenser

Referring now to the drawings, wherein like reference characters refer to like parts of the figures, a dispenser 10 is provided, generally comprising a liquid material 12 to be dispensed, a reservoir 14 which contains liquid material 12, a wick 16 made of pleated sheet material, an inner cage element 18, an outer cage element 20, a plunger rod 22, and a base element 24.

Figure 2:
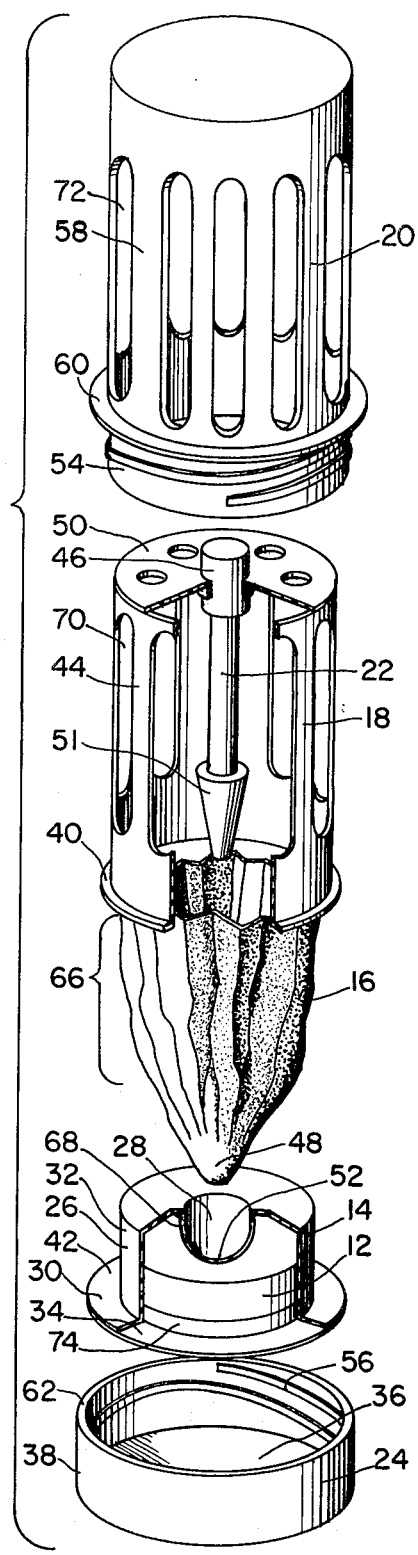
FIG. 2 is an exploded perspective view of the dispenser of FIG. 1, partially broken away and sectioned to show the individual elements comprising the dispenser as they appear prior to activation of the dispenser.

Reservoir 14 consists of an inverted cup 26, having a reentrant portion 28, a flange 30, and a cylindrical side wall 32. Base 34 is a solid disc of material which is sealed to flange 30, by gluing or other means. The reservoir 14 shown in FIG. 2, depicted before the dispenser 10 is actuated, is substantially sealed to prevent the liquid material 12 from spilling or evaporating before dispenser 10 is to be put into operation.

When the dispenser is assembled the lower face of base 34 is attached to surface 36 of base element 24 so that the side wall 32 of reservoir 14 is concentric to the side wall 38 of base element 24. The lower face of flange 40 of inner cage element 18 is then attached to the upper face 42 of flange 30 so that the cylindrical side wall 44 of inner cage element 18 is generally concentric to side wall 38 of base element 24.

The attachment of inner cage element 18 to upper face 42 of flange 30 captures wick 16 so that the foot portion 48 of wick 16 is within reentrant portion 28 of reservoir 14.

Upper end 46 of plunger rod 22 slidingly engages the top 50 of inner cage element 18; the lower, frustroconical end 51 of plunger rod 22 backs up foot portion 48 of wick 16 and lies within the depression defined by reentrant portion 28 of reservoir 14. Plunger rod 22 thus loosely holds foot portion 48 of wick 16 against the frangible bottom 52 of reentrant portion 28. In a preferred embodiment of the invention upper end 46 of plunger rod 22 is attached to top 50 of inner cage element 18 with a frangible joint which is broken when the dispenser 10 is actuated as described below.

Outer cage element 20 has a threaded lower edge 54, the threads of which engage the threaded inside surface 56 of side wall 38 of base element 24, so that inner and outer cage elements 18 and 20 are arranged with their respective side walls 44 and 58 generally concentric.

When the dispenser is to be actuated the outer cage element 20 is removed and the upper end 46 of plunger rod 22 is forced downward manually, which forces frustroconical end 51 of plunger rod 22, as well as the foot portion 48 of wick 16, against frangible bottom 52 of reentrant portion 28 with sufficient force to rupture frangible bottom 52 and force foot portion 48 of wick 16 into the interior portion of reservoir 14. Foot portion 48 of wick 16 is thus brought into contact with liquid material 12. Outer cage element 20 is then rethreaded onto the dispenser so that flange 60 of outer cage element 20 seats against seating rim 62 of base element 24. Actuation of dispenser 10 as described allows wicking of liquid material 12 from the interior of reservoir 14 to the remote portion 66 of the wick, which serves as the evaporative surface of the dispenser.

When the dispenser is in operation, as shown in FIG. 1, the side wall 68 of reentrant portion 28, being made of resilient material, resiliently engages the frustroconical end 51 of plunger rod 22, through foot portion 48 of wick 16, so that when the dispenser is in operation the liquid material 12 still within the reservoir 14 is isolated from the atmosphere to a large extent. This feature also prevents liquid material 12 from spilling from the dispenser 10 if the dispenser is waved to provide the "burst of deodorizing" described hereinafter.

When the dispenser is in operation the level of perfume diffusion may be adjusted by threading or unthreading outer cage element 20 slightly, with respect to inner cage element 18, to increase or decrease the registration between slots 70 of inner cage element 18 and slots 72 of outer cage element 20.

In one embodiment of the invention a signal fluid 74, immiscible with liquid material 12, may be provided in the dispenser 10. The function and desirability of a signal fluid to provide a run-out signal for the dispenser is specified below.

Selection of Perfume, Wick and Dispenser

In order for the liquid material diffusers of the present invention to work properly, the liquid material used therein should be formulated so that all its components, including the active ingredients, the base and any solvents, are within a narrow range of volatilities. Ideally, all of the components of the liquid material would be of equal volatility, so that the mixture would not fractionate during evaporation at all. A similar result would also be obtained if the entire liquid material composition was an azeotropic mixture. The ultimate liquid material would thus be made up of only one or only a few components. It will be recognized that there will be very few instances in which a perfume can be formulated with the appropriate odor characteristics using azeotropic mixtures or components of exactly the same volatility. The same problem is also noted in many other applications in which a liquid material is to be dispensed to the atmosphere. However, the closer the liquid material approaches a mixture having components which all have the same volatility, the less fractionation will be observed in the perfume composition.

In order to practice the present invention, it has been found to be important to choose for components of perfume compositions (or other multi-component liquids) a predominant amount of components which have moderate volatility as defined herein, and lesser amounts of materials with volatilities which are either greater or less than the range defined herein as a range of moderate volatility. In the present invention, the applicants have classified perfume materials into three categories of volatility by measuring the retention times for individual perfume components in a gas chromatograph. The details of this measurement are set forth below. Using the gas chromatograph retention times, the range of possible perfume components have been divided (as described previously) into low boilers or materials of high volatility; materials of moderate volatility; and high boilers or materials of low volatility.

It should be noted that in the determination of volatilities for individual perfume components, it will be found that many individual perfume components are themselves mixtures of materials of unknown composition. This problem is not uncommon in the perfume art, since many commercial or natural perfume materials contain components which cannot easily be identified and separated in order to determine the volatilities of the individual components. In such cases, the above determination of volatilities is made by running the retention time test for the multi-component perfume raw material of unknown composition. As a rough approximation, the gas chromatograph readout graph, made using the gas chromatograph conditions described below in the gas chromatograph retention time test, can be divided into the portion which represents a retention time of less than 16 minutes, the portion which represents a retention time of from 16 to 30 minutes, and the portion of the graph which represents a retention time of greater than 30 minutes. The areas under the peaks in each of these three regions can be summed in order to characterize the proportion of the material having a low volatility, and similarly, proportions of the material having moderate and high volatility. In calculating the proportion of materials in each of these volatility ranges the multi-component raw material can be treated as though it was three separate materials, each "material" representing one of the ranges of volatility. Using this method, it is possible in most cases to discover the proportions of low, moderate, and high volatility materials in virtually any perfume material which is capable of being passed through a gas chromatograph column.

What follows is a description of the stepwise process which one may use in order to select a perfume, a wick and a dispensing system as a particular embodiment of the present invention. An analogous process is followed when another type of liquid material is to be dispensed.

First, in practicing the present invention the perfumer will select a fragrance which he wishes to impart to the atmosphere. Similarly, a formulator of a nonperfume liquid material which is to be diffused to the atmosphere will have in mind certain criteria which the diffused material must meet. This parameter is first defined.

Next, the formulator will list potential materials which have an odor character or other property which is similar to the property desired to be imparted to the air from a diffusion dispenser. In the case of perfumes, this list will consist of all perfumes which have fragrances providing one or more notes of the desired final perfume.

The materials which are listed above are then analyzed to determine their gas chromatograph retention times, or ranges of retention times for components which are themselves mixtures. With these retention times in hand, the perfumer or formulator then formulates the final mixture, attempting, if possible, to formulate completely from those components which have been found to have a moderate volatility in terms of gas chromatograph retention time. Since it is frequently impossible to completely formulate a perfume which has no high boilers or low boilers in its composition, either as separate components or as impurities or fractions of the individual components, a minimal amount of materials of low or high volatility are selected to complete the perfume composition. The final composition should have less than 50% of materials of high volatility, which is to say that 50% to 100% of the composition should have a gas chromatograph retention time of at least 16 minutes. In preferred compositions less than 25% of the composition comprises materials having high volatility. At this stage, the percentage of components of low volatility is kept to an absolute minimum, since these high boilers are the components which can cause wick blockage and which are diffused to the atmosphere much more slowly than the preferred components of moderate volatility. Since the amount of these low volatility components in the claimed invention is determined with reference to the wick capacity for the overall perfume supply in a dispenser, it is not possible at this time to be sure that one's perfume is within the present invention. Thus, compliance with the proportion of materials of low volatility specified in the present invention is confirmed later in the process.

The next step in practicing the invention is to determine the rate at which the perfume is to be diffused to the atmosphere. Of course, the amount of material to be diffused by the dispenser per unit of time will depend on the concentration of liquid material which is to be imparted to the atmosphere, the volume of air to which the perfume is to be distributed in a given application, and the placement of the dispenser and the air circulation which will be encountered in the desired end use for the dispenser. The diffusion rate is best evaluated by placing a trial dispenser having a known diffusion rate for said perfume in place in an environment which simulates the situation in which the final dispenser will be used.

Once the desired diffusion rate for the perfume is known, the desired lifetime for the dispenser is selected. The product of the dispenser life and the rate of perfume diffusion provides the size of the perfume supply which must be placed in the reservoir in order to attain the desired dispenser life and diffusion rate characteristics.

Next, a suitable wick is selected for use in the invention. The wick is selected from sheet form materials, preferably materials having basis weights of from about 15 to about 50 grams per square meter of material. The wick absorptive capacity is measured, and should be within the range of from about 1.75 to 4.25 times the weight of the substrate for the perfume to be dispensed. A more preferred absorptive capacity is from about 2 to about 3 times the substrate weight for said perfume. The retention weight of said perfume in said wick substrate is also measured, and must be no more than about 10 milligrams of said perfume per square centimeter of said wick material.

Finally, diffusion efficiency of the selected wick for the perfume of choice is measured and the surface area of wick which must be saturated with the perfume and exposed to air in the dispenser is calculated by multiplying the trial dispenser evaporative surface area by the evaporative efficiency (measured according to the test below) of the trial dispensing wick, and dividing the result by the evaporative efficiency of the selected wick. Once this required evaporative surface area is defined for the selected wick, the total holding capacity (in grams) of the diffusion area for the perfume is determined. The weight of low volatility materials in the perfume composition is then multiplied by 100 times the reciprocal of 34%. If the resulting figure is greater than the holding capacity of the diffusion area, the perfume composition contains an excess of materials of low volatility, and the formula must be adjusted to correct this defect.

Next, the maximum vertical wicking height of the wick is measured, as well as the initial vertical wicking height. The initial vertical wicking height should be such that at least about 50% of the maximum wicking height is achieved within 3 minutes in order for the wick to be within the preferred embodiment of the present invention.

Finally, a dispenser is selected, and the distance down the wick from the bottom of the evaporative surface of the wick to the level of perfume in the dispenser is determined. This difference in length is then subtracted from the total wicking height in order to determine the height of wicking in the diffusion portion of the dispenser. The final dispenser can then be sized to provide the appropriate diffusion area for the system.

As a result of the multi-step selection process described above, a dispenser and perfume (or other liquid material) are provided which are compatible with each other and well suited for the intended end use of the dispenser. The perfume is formulated to achieve the desired odor intensity and character and to minimize fractionation, while the dispenser is designed to provide the perfume to the atmosphere at a chosen level for the desired length of time while further minimizing the fractionation of the perfume as it is diffused to the atmosphere. However, in some applications it will be desirable that the dispenser structure, the wick, or the perfume may be further optimized in order to meet a variety of optional objectives.

One additional feature which is highly desirable in dispensers of the present invention, although not in itself a part of the present invention, is the provision of a run-out signal in the dispenser. Dispensers of the type described are intended to be unobtrusive, and thus are expected to perform their function without much attention being directed to them. While the dispenser is in operation this state of affairs is highly desirable, but the attention of the consumer must be directed to the dispenser when the time to replace the dispenser is near, so that the dispenser will not run out and fail to provide the desired performance for a period of time before the consumer is able to obtain a replacement dispenser. Similarly, if the dispenser is designed to be refillable, the consumer must be informed when the dispenser is nearly ready to be refilled, so that the replacement perfume or wick materials may be obtained in order to replenish the dispenser before it is completely exhausted.

A preferred run-out signal for use herein is the provision of a color change in the wick to provide a clear visual indication of the imminence of product run-out. While the art describes various means to provide a run-out signal, the preferred method for indicating run-out is to provide in the dispenser a signal liquid which is not miscible with the perfume or other liquid material to be dispensed and which is adapted to be taken up by the wick and distributed to the visible portion thereof only after most of the active perfume or other liquid material has been passed through the evaporative surface of the wick. The essence of a functioning run-out signal of this type is that the perfume material is more compatible with the wick material than is the immiscible run-out signal. A specific example of an appropriate perfume material, wick, and signal fluid is the perfume of Composition B below, the Arkon II wick described below, and a signal fluid comprising ethylene glycol and 0.009% of FD and C Green No. 3 dye.

Another optional feature which may be provided in dispensers of the present invention is a temporary mode of dispenser operation in which the diffusion rate is increased by roughly two orders of magnitude over the steady state diffusion rate for the dispenser. This is useful because the steady state operation of the dispenser is intended to supply a level of perfume which is adequate for ordinary deodorizing or fragrance imparting needs, but not sufficient to deal with the sudden need for a higher level of perfume, for example, when a larger than usual quantity of a noxious odor is generated and must be dealt with.

The usual dispensers are not well adapted for this short term, high level diffusion of perfume. Rather, the typical dispenser is adapted to operate at a single diffusion rate.

This high diffusion rate in the short term may conveniently be provided by selecting wick material which is fairly permeable to air, and then selecting a dispenser design which allows the entire dispenser to be waved about in order to increase the contact between the perfume and the air sufficiently to provide what will be known hereinafter as a "burst of deodorizing" capability in the dispenser.

The two criteria which must be met in a dispenser which is to be used to provide a burst of deodorizing are as follows: First, the wick must have an air permeability of at least about 300 standard cubic feet per minute per square foot of wick surface area (about 92 standard cubic meters of air per minute per square meter of material); and, second, the dispenser should be designed so that liquid material in the reservoir is not easily spilled or shaken from the dispenser when it is waved back and forth manually. The latter characteristic is provided by the dispenser shown in the present specification, since the coaction of the plunger rod 23 and the side wall 68 of reentrant portion 28 is such that pooling of the perfume at this stricture is prevented. The dispenser is also designed so that perfume is not easily poured, inadvertently or otherwise, from the open portion of the reservoir.

Another feature which is optional in the present invention is the provision of means to vary the air flow to which the wick is exposed when the dispenser is at rest. The advantage of providing diffusion limitation means is that the perfume, wick and dispenser can be selected as described above in order to provide a level of diffusion which is more generous than is needed in the typical dispenser application. Thus, those consumers desiring to select a higher level of perfume distribution can open up the dispenser to allow maximum air flow across the wick, while those desiring a less potent level of perfume may rotate one of the cooperating cage elements so that the slits in the respective elements are partially or even completely out of registration. The art has long recognized that the provision of such flow limiting means is useful in order to allow the creation of a single dispenser which is useful to the widest number of consumers.

Test Methods

In the preceding part of the specification numerous tests are briefly identified which must be performed in order to practice the present invention. What follows is a complete description of each of these tests and the conditions under which they are conducted.

Wick Basis Weight Test

Basis weight is an art recognized term for the weight of a nonwoven or woven substrate per unit of area. Basis weight is measured herein as grams of material per square meter; the basis weight which is preferred herein for wick materials is from 15 to 50 grams per square meter, preferably from 17 to 35 grams per square meter of wick material.

In order to measure the basis weight of a material a sample measuring 10 centimeters by 10 centimeters is cut from the fabric to be tested. The sample is conditioned at a temperature of 23±1° C. and 50±2% relative humidity for 24 hours. The test is conducted under the same conditions of temperature and humidity. The sample is weighed on a conventional balance in grams, and the area is converted to square meters so that the number of grams per square meter is determined.

Total Absorptive Capacity Test

This test is used in order to determine the weight of a liquid material which can be absorbed by a given weight of wick material. The absorbent capacity is expressed as a multiple of the weight of dry substrate corresponding to the weight of liquid material absorbed. The test is conducted with the liquid material which is actually to be diffused to the atmosphere. The test is conducted as follows:

First, a sample is cut from the material to be tested. The sample should be a square strip which is 10 centimeters by 10 centimeters; the material is cut so that two opposed edges lie in the machine direction of the fabric and the other two opposed edges lie in the cross-machine direction. The samples are conditioned as described in the basis weight test, and the test is again conducted under those conditions.

Next, the weight of the material is determined.

Next, the sample is laid out horizontally on a sheet of nonabsorptive, impermeable and nonreactive sheet material. The liquid material selected is applied to the sample dropwise over its surface until the entire sample is supersaturated. The excess material is then blotted from the sample by laying the material for 10 seconds on a blotter made up of the same substrate material as the wick sample. The material is then flipped over and blotted on a new section of the same substrate for an additional 10 seconds. This saturated sample is then weighed, and the original sample weight is subtracted in order to determine the weight of liquid material absorbed by the wick. The liquid material weight is then divided by the dry substrate weight in order to determine the total absorbent capacity of the substrate sample.

Vertical Wicking Height and Initial Wicking Height Test

This test is adapted from the publication entitled "Liquid Wicking Rate: Capillary Test of Paper," *TAPPI Useful Methods*, 451.

The samples are first conditioned as above for 24 hours, and again the test is run under the same conditions of temperature and humidity. The samples cut for this test are rectangles which are 13 centimeters in the machine direction and 2.54 centimeters in the cross-machine direction. The sample is clamped at one of its shorter sides so that it hangs with the machine direction of the fabric essentially vertical. A millimeter scale is clamped adjacent and parallel to the sample so that the two nearly touch (but they are not permitted to touch during the test). The sample and rule are aligned so that the bottom edge of the sample strip is just below the zero mark of the graduated scale.

A reservoir of the liquid material is provided in a petri dish or like reservoir which has adequate holding capacity so that the liquid level will not be substantially diminished during the test. The clamped wick and rule are lowered toward the liquid surface in the reservoir so that the liquid level in the reservoir is at the zero mark on the millimeter scale when the lower extremity of the sample is just below the surface of the reservoir. A timer is started when the bottom of the sample first contacts the surface of the liquid in the reservoir.

The height of liquid in the wick is measured by comparing the height of the advancing head of liquid in the sample to the millimeter scale. Initial wicking height is the height of the head of liquid after 3 minutes have elapsed; total wicking height is defined herein as the height attained by the advancing head of liquid after 18 hours have elapsed.

Since evaporation of material from the wick may affect the results of the vertical wicking rate test, the test is conducted in a relatively draft-free environment. This may be provided by erecting a shield around the test apparatus, preferably a transparent shield so that the measurements can be made without disturbing it.

As already described, in order for the wick to be within the preferred mode of the present invention the initial wicking height must be at least about 50% of the total wicking height for substrates within the present invention.

Air Permeability Test

This test is necessary in the event that a dispenser is to be constructed which has the option of providing a burst of deodorizing. The air permeability of a dry substrate which is to be used in such an embodiment of the invention must be at least about 300 standard cubic feet of air per minute per square foot of material (92 standard cubic meters per minute per square meter of material) when measured in accordance with the present test. This test is an adaptation of ASTM Method D737-69, entitled "Standard Method of Test for Air Permeability of Textile Fabrics."

First, representative rectangular samples of a material, each measuring 10 centimeters on a side, are cut from the material to be tested.

The test is conducted using a Frazier air permeability testing apparatus, which is available from Frazier Precision Instruments Co., 210 Oakmont Avenue, Gaithersburg, Md.

Before using the Frazier apparatus, it is first tested for accuracy. The machine is leveled with respect to the lab bench. The test plate and corresponding nozzle to be used to calibrate the apparatus are then selected and attached to the testing apparatus. The pump and the apparatus are then started, and its pump speed is adjusted until the oil in the inclined manometer of the apparatus is raised to a level of 0.5 inches (1.27 centimeters). At this condition the oil level in the vertical manometer is observed and the air permeability without the substrate present is thus determined by consulting the tables for air permeability supplied with the machine. The Frazier machine is in a condition to conduct the air permeability test if the permeability of the machine without a sample in place is within 2% of the permeability value which is specified for the test plate.

Next, the test plate is removed and the sample to be tested is clamped to the Frazier machine in such a manner that the fabric is smooth and free from tension. The pump motor is started and the speed is adjusted until the oil level in the inclined manometer is steady at 0.5 inches (1.3 centimeters). The air permeability of the sample is measured by observing the level of oil in the vertical manometer and comparing the vertical manometer level with a calibration chart supplied with the machine in order to read out the air permeability of the sample. If the reading of the vertical manometer is not at least 3.0 inches (7.6 centimeters) a smaller nozzle must be selected in order to conduct the test properly.

Each sample is tested for air permeability at at least 5 locations on its surface; the multiple runs are then averaged to determine an average air permeability of the sample.

If one desires to determine the air permeability of a sample of the wick material which is saturated with the liquid material, the air permeability test may be run using a wick sample which is saturated with the liquid material and then blotted as described above in the absorbent capacity test.

The above air permeability readings are converted to standard readings (760 millimeters Hg pressure, 273.15° Kelvin) using the following formula:

$$(pv)/(t) = (PV)/(T)$$

in which p is the ambient atmospheric pressure in millimeters Hg at the time of the test, v is the number of cubic feet per minute measured on the Frazier machine, t is the ambient temperature of the test in degrees Kelvin, P is the standard pressure of 760 millimeters Hg, V is the air permeability in standard cubic feet per minute, and T is the temperature of 273.15° K. The equation may be substituted for the constant and rearranged to give the following equation for standard cubic feet per minute calculated from the measured cubic feet per minute:

$$V = \frac{pv(273.15° K.)}{t(760mm)} = \frac{.359 \, pv}{t}$$

To convert standard cubic feet per minute per square foot of material to standard cubic meters per minute per square meter of material, the permeability in standard cubic feet per minute per square foot is multiplied by 0.305.

Evaporative Efficiency Test

This test is used in order to compare the evaporation rate of a liquid material from a saturated wick with the evaporation rate of the same material from an open cup. The evaporative efficiency of the wick is obtained by defining the evaporation rate per unit area from an open cup as 1.00 units and then reporting the fraction of this unitary evaporation rate, per unit of surface area, which is achieved from a wick.

The evaporative efficiency test is conducted under standard temperature, pressure, and humidity conditions. Evaporation from the open cup and from the wick should be conducted at the same ambient conditions, and should be conducted at conditions which approximate the ambient conditions which will be observed when the wick and liquid material are in an operating dispenser.

First, an environment with a constant and reproducible air flow is created in which to conduct the test. The testing environment is an air supply sampling tube comprising a cylindrical glass funnel, preferably one having a diameter of about $4\frac{3}{4}$ inches (12 centimeters) inside diameter and a length of about 12 inches (31 centimeters). The funnel is reduced at its lower end to a tube with an inside diameter of about 0.9 centimeters. A cap is fabricated to fit over the open end of the funnel; the cap has a small exit port in its center which is about 0.7 centimeters in inside diameter. The cylindrical funnel is aligned with its long axis horizontal. An air compressor is connected to the tube at the lower end of the funnel to provide a steady level of airflow to the interior of the funnel. The air compressor is supplied with a needle valve so the flow rate can be adjusted to supply air to the sampling funnel at a rate of about 0.4 milliliters per second. The air flow is maintained at a steady rate throughout the experiment.

To insure that the flow rate is at the correct level and is constant over time, a side arm burette is connected to the outlet port of the air sampling tube, and a soap solution is placed in the portion of the burette just below the side arm. A rubber bulb is attached to the bottom of the burette so that the soap solution may be raised and lowered at will. The rate of air flow through the apparatus is then measured by depressing the bulb so that enough soap solution is adjacent to the side arm of the burette to form a bubble; the bubble is conveyed up the burette by the flow of air through the sampling tube, and the rate at which the bubble sweeps up the burette adjacent the volumetric markings of the burette is used to determine the flow rate and to adjust it to 0.4 milliliters per second.

The open cup evaporation rate is first measured. A sample of the selected liquid material is placed within an open cup which has vertical side walls and an exposed liquid surface area of about 10 square centimeters. A petri dish is ideal. The petri dish is filled with the selected liquid material to within about 6 millimeters of the top of its side wall so that the height of the side wall above the liquid surface level is minimized. The exact inside surface area is calculated by measuring the inside diameter of the petri dish.

The air flow in the horizontally disposed funnel is adjusted as described above so that the air flow rate is 0.4 milliliters per second. The sample is then weighed. This should be done just before the experiment is begun so that the liquid material in the petri dish has no substantial time to evaporate before the test is begun. The cover is removed from the open end of the cylindrical funnel and the sample is placed inside approximately centered lengthwise of the funnel, after which the cylindrical funnel is closed up and the starting time is noted. Fifteen minutes later the petri dish and sample are removed from the cylindrical funnel and immediately reweighed in order to determine the weight loss due to evaporation of a portion of the sample of liquid material. The open cup evaporation rate is reported as a weight loss during the test.

Next, the evaporation of material from a wick is conducted under identical experimental conditions. An initial sample of the substrate to be tested is cut with a surface area of about 40 square centimeters. The sample is supersaturated with the liquid material in the dropwise method described in the absorbent capacity test above. After the material is blotted as described in the same test, it is placed on a sheet of nonabsorptive, impermeable nonreactive sheet material (called "support material"), and the support material and saturated wick material sample are then weighed to provide an initial weight.

The support material and sample are placed within the cylindrical funnel and associated apparatus and exposed to the conditions described above for 15 minutes; the sample on the support material is then weighed in order to determine the weight loss due to evaporation of liquid material from the sample. If the total weight loss for the saturated sample is more than 10 milligrams different from the weight loss from the open cup, the substrate sample size is changed and the test is repeated until the weight loss from the substrate is nearly equivalent to the weight loss from the open cup.

The evaporative efficiency, E, of the wick sample is then calculated using the following formula:

$$E = (Wa)/(wA)$$

wherein w is the weight loss from the open cup, W is the weight loss from the substrate sample, a is the area of the liquid in the open cup and A is the evaporative surface area of the substrate. (Since one side of the wick is covered in this test, the evaporative surface area, A, is the same as the material surface area of the wick.)

Calculation of Retention Weight

One of the essential elements of the present invention is that the wick material must have a retention weight of less than 10 milligrams of the liquid material per square centimeter of evaporative surface. The retention weight is calculated by determining the total absorbency of the wick material for the liquid material as described above and determining the basis weight of the material. The total absorbency test is conducted with a sample of the wick material which has the same basis weight as the basis weight for which the retention time is calculated. The retention weight is simply the product of the sample basis weight and sample absorbent capacity, taking into account the fact that retention weight is expressed in milligrams per square centimeter, while basis weight is commonly expressed as grams per square meter.

Gas Chromatograph Retention Time

The gas chromatograph retention time of the individual materials in the perfume composition or other liquid material to be diffused is the lapse in time between the time of introduction of a sample into a gas chromatograph column and the time of the individual component exiting from the gas chromatograph and being detected by a detector. With proper gas chromatograph column selection, the length of the retention time is closely correlated to the volatility of the component. This method is selected in preference to the estimation of volatilities by measuring the boiling points of individual perfume materials, since many of the perfume raw ingredients are not easily separated into individual components so that the individual boiling points can be measured.

The apparatus used to measure retention time is a Hewlett-Packard Model 5830A gas chromatograph. The chromatograph column used for this purpose is a 10 foot length by ⅛ inch diameter stainless steel column packed with 10% SP-1000 stationary phase on 100/120 Chromosorb WAW support. This column is sold as Catalog No. 1-2197 by Supelco, Inc., Bellefonte, Pa. 16823. The gas chromatograph is operated at an injection port temperature of 250° C. and a flame ionization detector temperature of 300° C. The carrier gas is helium, supplied at the rate of 21 millimeters per minute.

When the gas chromatograph is to be used, the column is first heated to a temperature of 70° C., at which time a retention time measurement is begun. The column temperature is then increased at the rate of 4° C. per minute until the final temperature of 260° C. is reached; the column is then held at 260° C. during the remainder of the test (total test time was 75 minutes).

A particular material to be analyzed for its retention time is injected into the column at an initial time which is noted on the recording chart. The sample diffuses through the column and when it leaves the other end of the column it is detected by a flame ionization detector, appearing as a peak on the chromatograph chart. The time between injection and the appearance of the peak is automatically printed on the chart. When the component is a pure compound the retention time is expressed as a single time. However, in many cases the individual materials to be tested for retention time will each be a mixture of materials, the composition of which is unknown. The retention time will then be a series of peaks representing the retention time of each individual component of the particular perfume ingredient. If a substantial fraction or nearly all of the peaks are classified in a single volatility range, the material is classified as belonging to that volatility range, even though it is not a single material. In the event that the retention times of the individual peaks span a broad range of volatilities, the peaks may be analyzed so that a proportion of peak area is recorded for each of the volatility ranges specified. The material is then characterized as having one percentage of low boilers, another percentage of materials of moderate volatility, and a third percentage of high boilers. The retention time characteristics of each of the individual components of the liquid material are analyzed as described, and the retention time characteristics of each are then used in the formulation of liquid materials as described above.

Desired Perfume Diffusion Rate Test

The perfume or liquid material diffusion rate which is desired in a given dispenser application is measured by calculating how much perfume is to be dispensed per unit time in a given environment in order to maintain a desirable perfume concentration in the environment in which the dispenser is to be used. The desired concentration of the liquid material is easily measured by diffusing the material in varying amounts to a test room until a concentration is found which provides the desired fragrance or other property. In case of perfumes, this concentration is found by having subjects enter test rooms which each contain a dispenser which provides perfume at a known diffusion rate and having the subjects choose the room providing the level of diffusion which they prefer. The results for the subjects are averaged in any way desired in order to define a typical dispensing level to be attained.

EXAMPLE

This example describes how the preferred dispenser, perfume and wick were selected in order to produce the best mode of the present invention.

The objective was to diffuse a citrus type fragrance in the environment of a small household room. Perfume materials were selected which provide citrus-type notes and other notes necessary for the perfume, and the retention times and retention time ranges for the various components were measured. These measurements are provided in Table 1 below for the perfume ingredients chosen for formulating perfume compositions. (In Table 1 retention times are specified for each principal peak of the ingredients containing more than one chemical compound.)

TABLE 1

| Material | Retention Times of Major Components (Min.)* | Retention Times of Minor Components (Min.)* |
|---|---|---|
| Allyl caproate | 16.2 | |
| Allyl cyclohexene propionate | 28.8 | |
| Benzyl alcohol | 29.5 | |
| Cis-3-hexenyl acetate | 14.0 | |
| Citral | 24.8, 26.2 | |
| p-Cymene | 13.6 | 5.3, 5.7 |
| Decyl aldehyde | 18.6 | 25.7, 33.3, 43.2 |
| Dihydromyrcenol | 17.9 | 24.2 |
| 2,6-Dimethylhepten-2-al(7) | 13.7, 14.4 | 17.2, 17.5, 19.9, 21.1 |
| Eucalyptol | 10.1 | 5.3, 11.7, 22.6, 23.7 |
| Geraniol | 28.7 | 27.5 |
| Isobornyl acetate | 22.8 | 20.6, 24.7 |
| Lavandin | 20.5, 21.5 | 11.4, 25.2 |
| Lemon terpenes | 10.4 | 5.8, 8.0, 11.7 |
| Limettal** | 26.3, 28.5, 32.4 | 11.7, 52.4 |
| Linalool | 19.2 | |
| Linalool oxide | 18.0, 18.9 | 20.7, 25.0 |
| Linalyl acetate | 21.5 | |
| Methyl benzoate | 22.5 | |
| Methyl nonyl acetaldehyde | 23.5 | 22.7 |
| Nerol oxide | 18.5 | 16.2, 20.0 |
| Octyl aldehyde | 12.3 | |
| Orange terpenes | 10.4 | 5.8, 8.0 |
| Peppermint | 10.3, 18.1, 22.8 | 10.3–41.0 |
| β-pinene | 8.2 | |
| Rose oxide | 15.9 | 16.4 |
| Spearmint | 26.6 | 5.8–23.0 |
| Terpinolene | 6.6, 10.7, 11.4, 13.9, 25.7 | 6.6–29.7 |

*Retention times can vary ± 1 minute due to column variation (several columns were used during the study).
**Sold by Naarden International, 919 Third Avenue, New York, New York 10022.

After having studied the retention time information collected, and considering also the methodology of the perfume art, two trial perfume compositions were formulated. These compositions are denoted as A and B below:

| COMPOSITION A | |
|---|---|
| Component | Wt. % |
| Linalool | 17.64 |
| Linalyl Acetate | 17.64 |
| 2,6-Dimethylhepten-2-al(7) | 1.76 |
| Allyl cyclohexene propionate | 14.11 |
| Octyl aldehyde | 0.35 |
| Decyl aldehyde | 1.76 |
| Citral | 17.64 |
| Dihydromyrcenol | 15.87 |
| Lavandin | 5.30 |
| Methyl nonyl acetaldehyde | 5.30 |
| Peppermint | 0.88 |
| Cis-3-hexenyl acetate | 0.35 |
| Rose oxide | 0.35 |
| Linalool oxide | 0.35 |
| Limettal | 0.35 |
| Nerol oxide | 0.35 |
| | 100.00 |

| COMPOSITION B | |
|---|---|
| Component | Wt. % |
| Orange terpenes | 28.3 |
| Lemon terpenes | 10.0 |
| Terpinolene | 5.0 |
| Linalool | 10.0 |
| Linalyl acetate | 10.0 |
| 2,6-Dimethylhepten-2-al(7) | 1.0 |
| Allyl cyclohexene propionate | 8.0 |
| Octyl aldehyde | 0.2 |
| Decyl aldehyde | 1.0 |
| Citral | 10.0 |
| Dihydromyrcenol | 9.0 |
| Lavandin | 3.0 |
| Methyl nonyl acetaldehyde | 3.0 |
| Peppermint | 0.5 |
| Cis-3-hexenyl acetate | 0.2 |
| Rose oxide | 0.2 |
| Linalool oxide | 0.2 |
| Limettal | 0.2 |
| Nerol oxide | 0.2 |

| COMPOSITION B | |
|---|---|
| Component | Wt. % |
| | 100.0 |

(0.1% BHT was also added to both compositions above in order to prevent oxidation.)

Composition A contains only very small amounts of materials having retention times less than 16 minutes or more than 30 minutes. Composition B contains about 43% of materials having retention times less than 16 minutes and only very small amounts of materials with retention times greater than 30 minutes.

The desired rate of delivery of each perfume in the atmosphere was then measured. This was done by diffusing perfume at a known rate in a closed room and allowing people to enter the room and decide whether the perfume was too strong, acceptable, or too weak. The results of many such tests were averaged, and the desired perfume delivery rates were 3.45 and 6.25 milligrams per hour for Compositions A and B, respectively.

A dispenser lifetime of 28 days was chosen, so that the total amount of perfume to be delivered to the dispenser would be about 2.3 and 4.2 grams of material for Compositions A and B, respectively.

Next, a wick was selected for use to evaporate perfume materials of the present invention.

Of the numerous substrates tested, three particular wick substrates were found which were particularly useful herein. The first such substrate is identified as Model No. S0707147, sold by Arkon Corporation, 315 Pendleton Rd., Greenville, S.C. 29601. This material, known as the "Arkon I" substrate hereinafter, comprises 100% rayon fiber having a denier of about 1.5. Arkon I is bound with TR653 binder provided by the Rohm and Haas Company, Philadelphia, Pa. A second wick material useful herein is the Arkon substrate identified as Model No. 0802184-CC, known hereafter as Arkon II. This material is identical to the Arkon I wick material, except that it is bound with HA8 binder available from the Rohm and Haas Company. A third substrate useful herein is style 479.32 substrate available from the Kendall Corporation, 1 Federal Street, Boston, Mass. 02110. This material is known hereinafter as Kendall. This material also is comprised of 100% rayon fiber of a denier of 1.5; Kendall is bound with E-32 binder available from Rohm and Haas. These materials are more completely characterized in Table 2 below which provides the basis weight, absorbent capacity and retention weight of the wick materials; Table 3 below which provides the evaporative efficiency of each substrate; and Table 4 which provides the air permeability of the dry and saturated substrates. The material used as the liquid material where necessary in the tests was Composition B above. All tests were performed in accordance with the test methods described above.

TABLE 2

| Substrate | Basis Weight | Absorptive Capacity | Retention Weight |
|---|---|---|---|
| Arkon I | 33.7 | 3.35 | 5.64 |
| Arkon I | 34.0 | 3.14 | 5.33 |
| Arkon I | 37.2 | 3.05 | 5.68 |
| Kendall | 31.0 | 2.23 | 3.46 |
| Kendall | 31.0 | 2.25 | 3.48 |
| Kendall | 31.2 | 1.95 | 3.05 |
| Arkon II | 44.9 | 4.19 | 9.41 |

TABLE 2-continued

| Substrate | Basis Weight | Absorptive Capacity | Retention Weight |
|---|---|---|---|
| Arkon II | 47.6 | 3.98 | 9.49 |

TABLE 3

| Substrate | Evaporative Rate (mg/hr cm$^2$) | Evaporative Efficiency |
|---|---|---|
| Open cup | 13.73 | 1.000 |
| Arkon I | 2.98 | 0.217 |
| Arkon II | 2.88 | 0.210 |
| Kendall | 2.28 | 0.166 |

TABLE 4

| Substrate | Dry | Saturated |
|---|---|---|
| Arkon I | 468 CFM/ft$^2$ | 222 CFM/ft$^2$ |
| Arkon II | 369 CFM/ft$^2$ | No flow |
| Kendall | 417 CFM/ft$^2$ | 165 CFM/ft$^2$ |

For the above wicks the absorbent capacities were between 1.75 and 4.25 times the weight of the substrate and the retention weight of Composition B in the substrate was less than 10 milligrams per square centimeter of material. It was found that a total wick surface evaporative area of about 270 square centimeters of any of the substrates in Table 4 would be required in order to dispense the appropriate level of the liquid perfume of Composition B in the chosen environment of use.

Composition B contained about 0.7% low volatility materials, and the calculated amount of perfume to be added to the reservoir was about 4.2 grams, so the amount of high boiling materials in the perfume supply in this example was about 0.03 grams. Based on the product of the retention weight and the total evaporative surface required, the total amount of high boilers in the perfume supply was about 2% of the holding capacity of the evaporative portion of the wick, so this met the requirement of the present invention that the total amount of high boilers in the composition be less than one-third of the holding capacity of the evaporative area of the wick.

Next, the wicking height and the initial wicking height was determined for each of the selected wick substrates. Those values are reported in Table 5 below:

TABLE 5

| Substrate | Initial Wicking Height | Wicking Height |
|---|---|---|
| Arkon I | 4.60 cm. | 9.20 cm. |
| Arkon II | 6.03 cm. | 7.62 cm. |
| Kendall | 3.97 | 8.10 cm. |

It will be noted that the initial wicking height measured at 3 minutes was at least 50% of the total wicking height after 18 hours had elapsed, for the Arkon I and II wicks.

A dispenser according to the description of FIGS. 1 and 2 was constructed using the Arkon I substrate as a wick. In this dispenser embodiment the maximum possible wick height was limited to 7.0 centimeters by the physical dimensions of the dispenser parts, so total vertical wicking height of any of the indicated substrates was not the limiting factor in determining the vertical extent of the wick. The distance from the bottom of the reservoir to the lower extremity of the evaporative surface of the dispenser was 1.9 centimeters, leaving a maximum vertical extent of 5.1 centimeters for the evaporative surface of the wick.

The wick used in this dispenser was cut as a disc having a radius of 7.0 centimeters, and the portion of the wick residing within the reservoir when the dispenser was in use was a central disc segment of the wick having a radius of 1.9 centimeters, so the evaporative surface in this embodiment of the invention was an annulus having a sheet surface area of roughly 135 cm$^2$. Since both sides of the wick were exposed to the atmosphere, the evaporative surface area of the wick was twice 135 cm$^2$, or about 270 cm$^2$.

What is claimed is:

1. A liquid perfume dispenser comprising a supply of a volatizable multi-component liquid perfume to be dispensed at a desired diffusion rate, a reservoir which maintains said perfume supply in isolation from ambient air, and a sheet form wick having a foot portion which contacts said isolated liquid perfume supply and wherein said wick has a remote portion providing an evaporative surface in contact with the ambient air, wherein:

A. said remote portion has a retention weight no more than 10 milligrams of said perfume per square centimeter of said evaporative surface; and wherein said remote portion has an absorptive capacity of from about 1.75 to about 4.25 times its weight of said perfume and wherein the basis weight of said remote portion is from 15 to 50 grams per square meter; and wherein said remote portion has a vertical wicking height of at least 5 centimeters; and B. wherein said liquid perfume supply comprises a multi-component liquid selected from the group consisting of high, low and moderate volatility materials, wherein 50% to 100% by weight of said perfume supply materials is of low and moderate volatility; wherein the total weight of said low volatility materials in said perfume supply is no more than 34% of the holding capacity of said remote portion of said wick, and wherein said dispenser and said multi-component perfume to be dispensed maintains in said remote portion a relatively constant composition of said multi-component liquid, and wherein said multi-component liquid evaporates at a relatively steady rate over the life of the dispenser.

2. The dispenser of claim 1, wherein 75% to 100% of said liquid material supply comprises materials of low and moderate volatility.

3. The dispenser of claim 1, wherein said remote portion has the ability to achieve at least about 50% of said vertical wicking height in 3 minutes.

4. The dispenser of claim 3, wherein said remote portion has an absorptive capacity of from 2 to 3 times its weight of said liquid, a basis weight of 17 to 35 grams per square meter and a vertical wicking height of at least 7.5 centimeters.

5. The invention of claim 2, wherein said wick has an air permeability in its dry state of at least about 92 standard cubic meters per square meter of material per minute.

6. The invention of claim 2, wherein said liquid material consists essentially of materials of moderate volatility.

* * * * *